(12) United States Patent
Wei et al.

(10) Patent No.: US 9,056,028 B2
(45) Date of Patent: Jun. 16, 2015

(54) DRYNESS INDICATOR FOR AN ABSORBENT ARTICLE

(75) Inventors: Ning Wei, Roswell, GA (US); Shiming Zhuang, Menasha, WI (US); Xuedong Song, Alpharetta, GA (US); Kimberly Nicole Struk, Richfield, MN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 429 days.

(21) Appl. No.: 13/459,834

(22) Filed: Apr. 30, 2012

(65) Prior Publication Data
US 2013/0289508 A1 Oct. 31, 2013

(51) Int. Cl.
*A61F 13/15* (2006.01)
*A61F 13/42* (2006.01)
*G04F 13/06* (2006.01)

(52) U.S. Cl.
CPC ................. *A61F 13/42* (2013.01); *G04F 13/06* (2013.01); *A61F 2013/423* (2013.01); *A61F 2013/422* (2013.01)

(58) Field of Classification Search
CPC .... A61F 13/42; A61F 2013/422; G04F 13/06
USPC ..................... 604/361; 600/362; 116/206, 200
See application file for complete search history.

(56) References Cited

U.S. PATENT DOCUMENTS

| | | | |
|---|---|---|---|
| 4,229,813 A | 10/1980 | Lilly et al. | |
| 4,408,557 A | 10/1983 | Bradley et al. | |
| 4,507,121 A | 3/1985 | Leung | |
| 5,058,088 A | 10/1991 | Haas et al. | |
| 6,741,523 B1 | 5/2004 | Bommarito et al. | |
| 6,916,116 B2 | 7/2005 | Diekmann et al. | |
| 7,232,253 B2 | 6/2007 | Isbitsky et al. | |
| 7,280,441 B2 | 10/2007 | MacDonald et al. | |
| 7,362,663 B2 | 4/2008 | Kagan | |
| 7,388,814 B2 | 6/2008 | Teffenhart et al. | |
| 7,569,185 B2 | 8/2009 | Fischer | |
| 7,643,378 B2 | 1/2010 | Genosar | |
| 7,834,234 B2 | 11/2010 | Roe et al. | |
| 8,053,625 B2 | 11/2011 | Nhan et al. | |
| 2006/0264858 A1 | 11/2006 | Roe et al. | |
| 2007/0092451 A1 | 4/2007 | Loveridge et al. | |

(Continued)

FOREIGN PATENT DOCUMENTS

GB 2459317 A 10/2009
WO WO 03/07088 A2 1/2003

(Continued)

*Primary Examiner* — Melanie Hand
*Assistant Examiner* — Aundria Hairell
(74) *Attorney, Agent, or Firm* — Kimberly-Clark Worldwide, Inc.

(57) ABSTRACT

A dryness indicator includes a wicking strip continuous between a reservoir end and an opposed open end; a liquid-impermeable top layer disposed on one side of the wicking strip; and a liquid-impermeable bottom layer disposed on the opposite side of the wicking strip, wherein the top layer is affixed to the bottom layer to at least partially enclose the wicking strip, and wherein the indicator is configured such that the open end of the wicking strip can be placed in liquid communication with an object or surface. The dryness indicator also includes a reservoir including an oil-based colorant with the potential to be in liquid communication with the reservoir end of the wicking strip, wherein the wicking strip is configured such that colorant wicking from the reservoir end and an unreacted water-based fluid wicking from the open end meet to define a timing line.

19 Claims, 9 Drawing Sheets

(56) References Cited

U.S. PATENT DOCUMENTS

| | | |
|---|---|---|
| 2008/0025154 A1* | 1/2008 | MacDonald et al. ........... 368/89 |
| 2008/0228157 A1 | 9/2008 | McKiernan et al. |
| 2009/0157022 A1 | 6/2009 | MacDonald et al. |
| 2009/0221980 A1 | 9/2009 | Mosbacher et al. |
| 2010/0108555 A1 | 5/2010 | Genosar |
| 2010/0221678 A1 | 9/2010 | Fischer |
| 2011/0204762 A1 | 8/2011 | Eubanks et al. |

FOREIGN PATENT DOCUMENTS

| | | |
|---|---|---|
| WO | WO 2007/050281 A2 | 5/2007 |
| WO | WO 2009/127867 A1 | 10/2009 |

* cited by examiner

DRYNESS INDICATOR FOR AN ABSORBENT ARTICLE

BACKGROUND

Absorbent articles such as diapers, training pants, incontinence products, feminine hygiene products, swim undergarments, and the like, conventionally include a liquid permeable body-side liner, a liquid impermeable outer cover, and an absorbent core. The absorbent core is typically located between the outer cover and the liner for taking in and retaining liquids (e.g., urine) exuded by the wearer. The absorbent core can be made of, for instance, superabsorbent particles. Many absorbent articles are so efficient at absorbing liquids that it is sometimes difficult to tell whether or not the absorbent article has been insulted with a body fluid, or when such an insult has occurred.

Accordingly, various types of moisture or wetness indicators have been suggested for use in absorbent articles. The wetness indicators may include alarm devices that are designed to assist parents or attendants in identifying a wet diaper condition early on. These devices produce either a visual or an audible signal. Many of these devices rely on electronics and/or chemicals, which may increase the expense of the absorbent article. Further, electronic devices rely on electrical sources and may be prone to failure if utilized for an extended period of time.

Problems, however, have been encountered in designing a signaling device that does not appreciably increase the cost of the absorbent article, while providing a meaningful signal to the caregiver without relying on an electrical or chemical source for operation.

SUMMARY

The present inventors undertook intensive research and development efforts concerning improving absorbent articles, particularly with respect to providing a simple wetness/dryness indicator. The present disclosure presents a solution to the problems described above by providing a wetness/dryness indicator that is responsive without electronics or chemicals. The indicator needs only a small quantity of liquid insult to present an indication visible to the caregiver or wearer of the absorbent article while at the same time avoiding complex chemical or electrical indicators.

This indicator provides additional information to a caregiver that can be particularly useful during toilet training. The indicator can indicate wetness, but can also indicate how long the diaper or training pant remained dry before it was wet. Such a product provides significant benefit to caregivers because it can provide information about a baby's development process (such as urine holding time) and the baby's readiness for potty training.

A dryness indicator includes a wicking strip continuous between a reservoir end and an opposed open end; a liquid-impermeable top layer disposed on one side of the wicking strip; and a liquid-impermeable bottom layer disposed on the opposite side of the wicking strip, wherein the top layer is affixed to the bottom layer to at least partially enclose the wicking strip, and wherein the indicator is configured such that the open end of the wicking strip can be placed in liquid communication with an object or surface. The dryness indicator also includes a reservoir including an oil-based colorant with the potential to be in liquid communication with the reservoir end of the wicking strip, wherein the wicking strip is configured such that colorant wicking from the reservoir end and an unreacted water-based fluid wicking from the open end meet to define a timing line.

A hydraulically-controlled dryness indicator includes a wicking strip continuous between a reservoir end and an opposed open end, wherein the indicator is configured such that the open end of the wicking strip can be placed in liquid communication with an object or a surface; and a reservoir including an oil-based colorant with the potential to be in liquid communication with the reservoir end of the wicking strip, wherein the wicking strip is configured such that colorant wicking from the reservoir end and unreacted water-based fluid wicking from the open end meet to define a timing line, and wherein the wicking strip is free of substances with which the unreacted water-based fluid can react.

A disposable absorbent article for absorbing a liquid includes a chassis including a liner, an outer cover, and an absorbent structure positioned between the liner and the outer cover, the chassis including a crotch region positioned in between a front region and a back region, the front region and the back region defining a waist region therebetween. The article also includes a dryness indicator positioned adjacent the liner or the outer cover, the dryness indicator including a wicking strip continuous between a reservoir end and an opposed open end; a liquid-impermeable top layer disposed on one side of the wicking strip; and a liquid-impermeable bottom layer disposed on the opposite side of the wicking strip, wherein the top layer is affixed to the bottom layer to at least partially enclose the wicking strip, and wherein the indicator is configured such that the open end of the wicking strip can be placed in liquid communication with a disposable absorbent article. The dryness indicator also includes a reservoir including an oil-based colorant with the potential to be in liquid communication with the reservoir end of the wicking strip, wherein the wicking strip is configured such that colorant wicking from the reservoir end and unreacted urine wicking from the open end meet to define a timing line.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings.

Repeat use of reference characters in the present specification and drawings is intended to represent the same or analogous features or elements of the present disclosure.

DETAILED DESCRIPTION

It is to be understood by one of ordinary skill in the art that the present discussion is a description of exemplary aspects only, and is not intended as limiting the broader aspects of the present disclosure.

The present disclosure is generally directed to absorbent articles adapted to indicate the presence of a body fluid in the absorbent article or other changes in the condition of the product or wearer. The absorbent article may be, for instance, a diaper, a training pant, an incontinence product, a feminine hygiene product, a medical garment, a bandage, or the like. Generally, the absorbent articles are disposable, meaning that they are designed to be discarded after a limited use rather than being laundered or otherwise restored for reuse.

Figure 1:
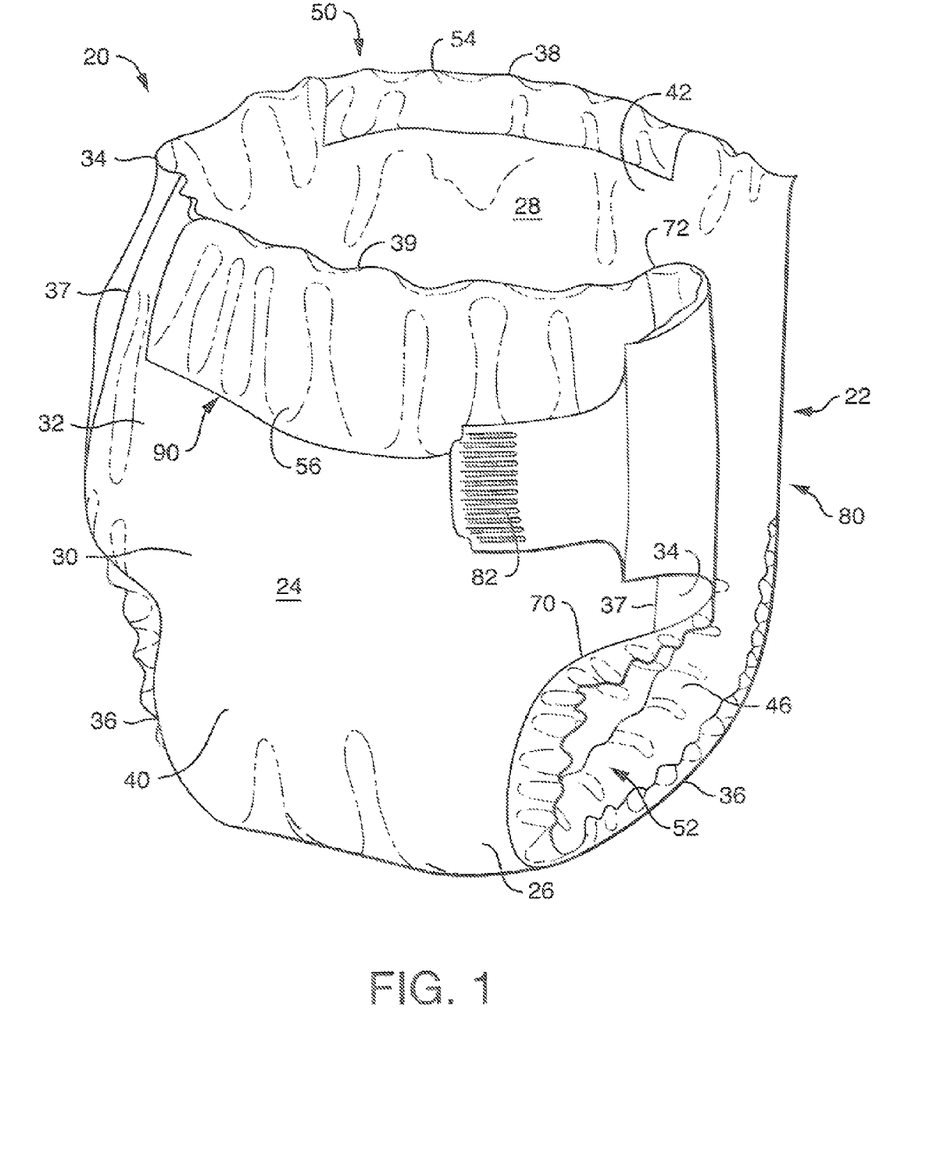
FIG. 1 is a rear perspective view of one aspect of an absorbent article.
Figure 2:
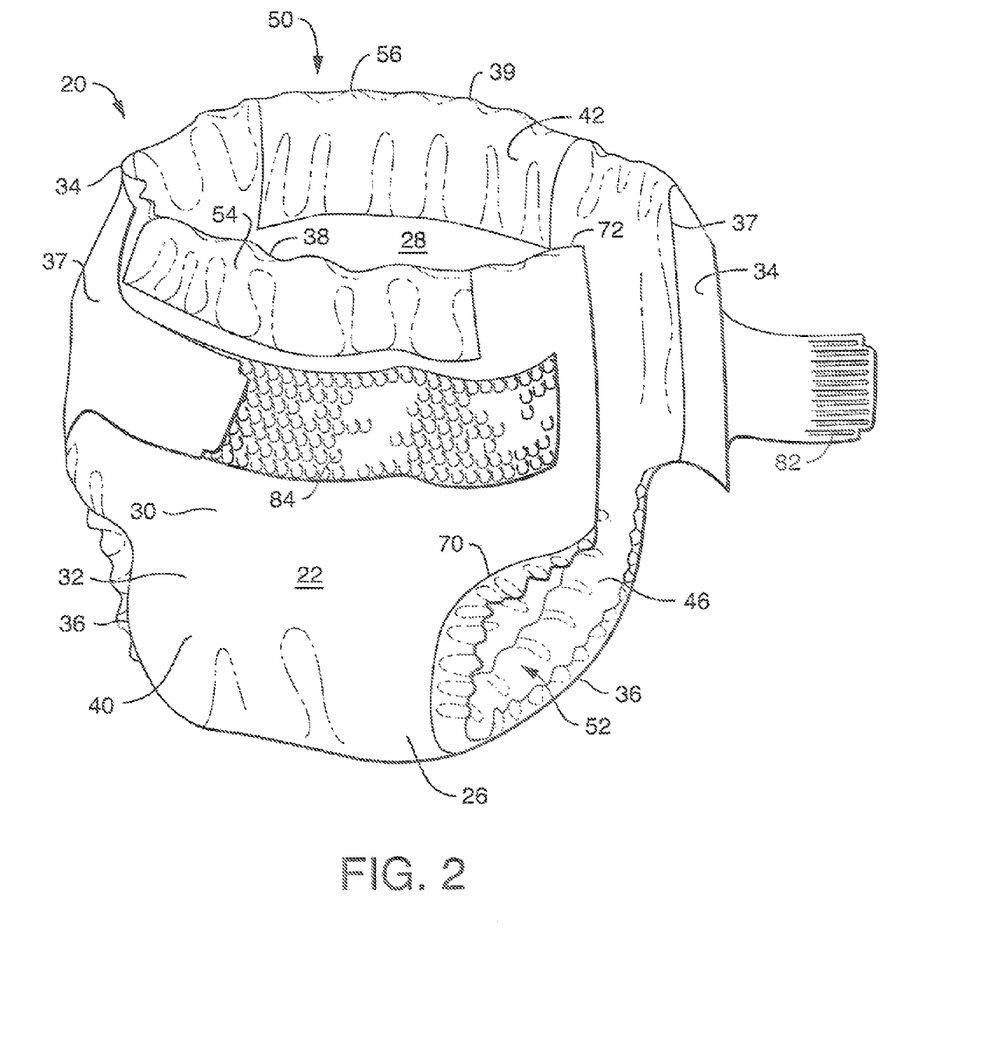
FIG. 2 is a front perspective view of the absorbent article illustrated in FIG. 1.

Referring to FIGS. 1 and 2, for exemplary purposes, an absorbent article 20 that may be made in accordance with the present disclosure is shown. The absorbent article 20 may or may not be disposable. It is understood that the present disclosure is suitable for use with various other absorbent articles intended for personal wear including, but not limited to, diapers, training pants, swim pants, feminine hygiene products, incontinence products, medical garments, surgical pads and bandages, other personal care or health care garments, and the like, without departing from the scope of the present disclosure.

By way of illustration only, various materials and methods for constructing absorbent articles such as the diaper 20 of the various aspects of the present disclosure are disclosed in PCT Patent Application WO 00/37009 published Jun. 29, 2000 by A. Fletcher et al.; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
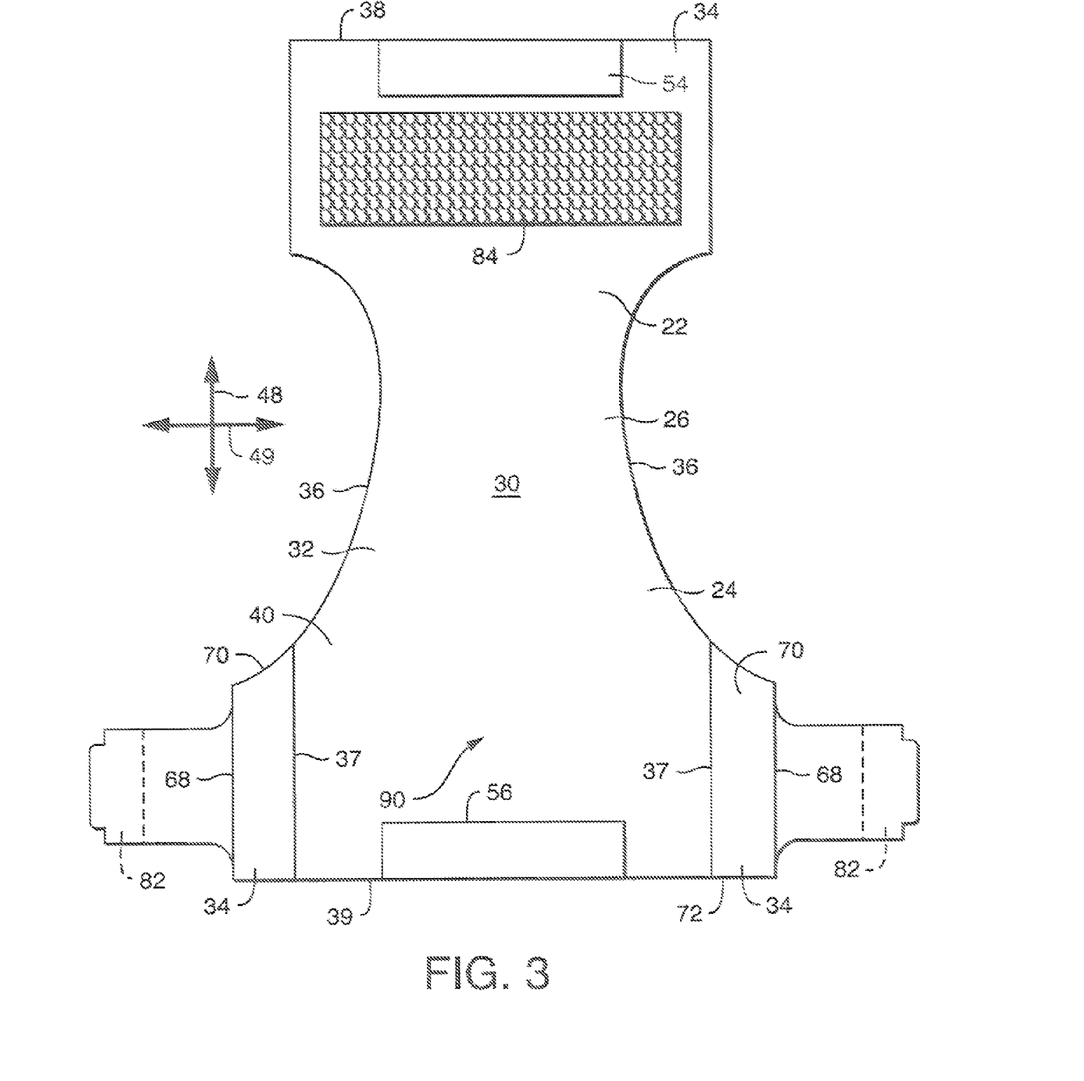
FIG. 3 is a plan view of the absorbent article shown in FIG. 1 with the article in an unfastened, unfolded and laid flat condition showing the surface of the article that faces away from the wearer.
Figure 4:
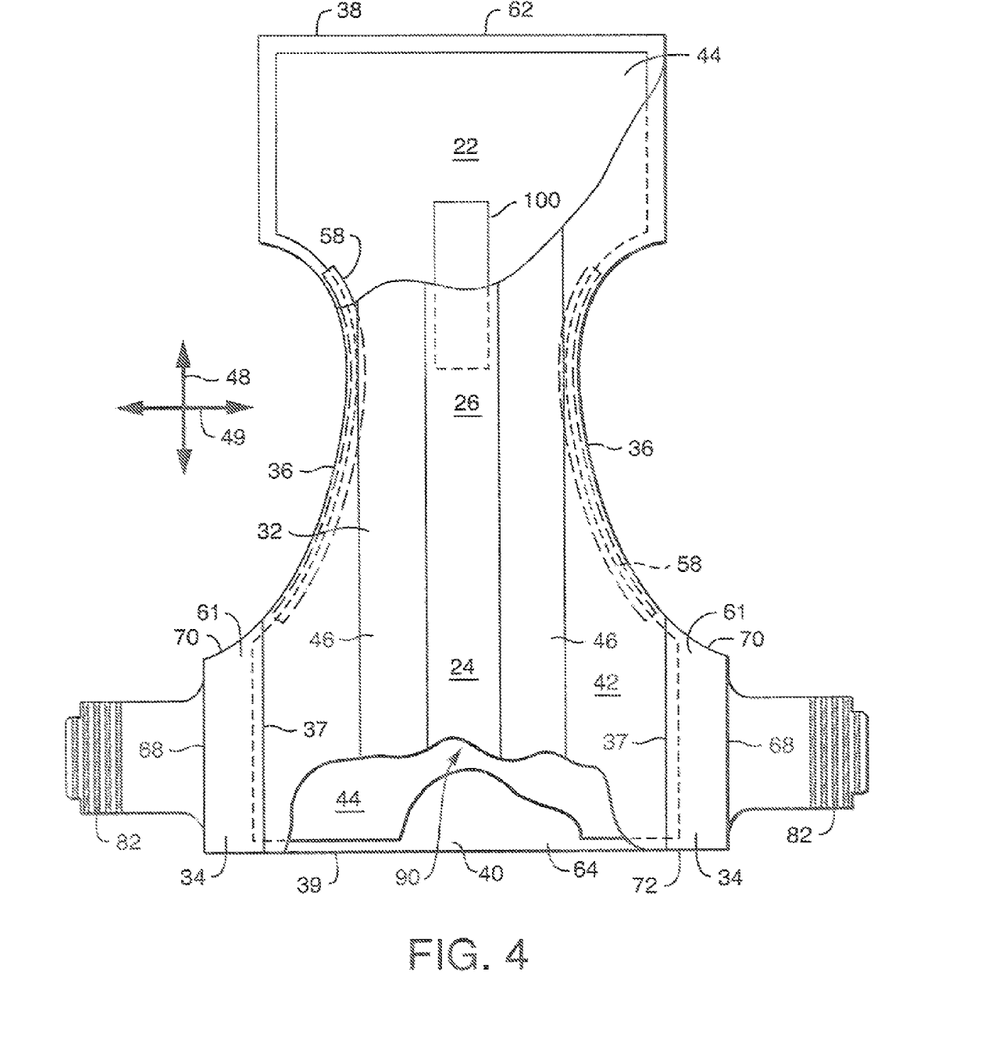
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article, when worn. to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20 which, when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this aspect, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during use of the absorbent article 20. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example, with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some aspects, the absorbent article 20 may further include a surge management layer 60 that may be optionally located adjacent the absorbent structure 44 and attached to various components in the article 20, such as the absorbent structure 44 or the bodyside liner 42, by methods known in the art, such as by using an adhesive. A surge management layer 60 helps to decelerate and diffuse surges or gushes of liquid that may be rapidly introduced into the absorbent structure 44 of the article 20. Desirably, the surge management layer 60 can rapidly accept and temporarily hold the liquid prior to releasing the liquid into the storage or retention portions of the absorbent structure. Examples of suitable surge management layers 60 are described in U.S. Pat. No. 5,486,166 issued Jan. 23, 1996 to David F. Bishop et al. and U.S. Pat. No. 5,490,846 issued Feb. 13, 1996 to Clifford J. Ellis et al. Other suitable surge management materials are described in U.S. Pat. No. 5,820,973 issued Oct. 13, 1998 to Richard N. Dodge II et al. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown, particularly in FIGS. 1 and 2, the side panels 34 may be stretched around the waist and/or hips of a wearer in order to secure the garment in place. As shown in FIGS. 3 and 4, the elastic side panels 34 are attached to the chassis 32 along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative aspect, the elastic side panels 34 may also be integrally formed with the chassis 32. For instance, the side panels 34 may comprise an extension of the bodyside liner 42, of the outer cover 40, or of both the bodyside liner 42 and the outer cover 40.

In the aspects shown in the figures, the side panels 34 are connected to the back region 24 of the absorbent article 20 and extend over the front region 22 of the article 20 when securing the article 20 in place on a user. It should be understood, however, that the side panels 34 may alternatively be connected to the front region 22 of the article 20 and extend over the back region 24 when the article 20 is donned.

With the absorbent article 20 in the fastened position as partially illustrated in FIGS. 1 and 2, the elastic side panels 34 may be connected by a fastening system 80 to define a three-dimensional diaper configuration having a waist opening 50 and a pair of leg openings 52. The waist opening 50 of the article 20 is defined by the waist edges 38 and 39 which encircle the waist of the wearer.

In the aspects shown in the figures, the side panels 34 are releasably attachable to the front region 22 of the article 20 by the fastening system 80. It should be understood, however, that in other aspects, the side panels 34 may be permanently joined to the chassis 32 at each end. The side panels 34 may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article 20. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge 70 of the back region 24, or alternatively, neither of the leg end edges 70 may be curved or angled, without departing from the scope of the present disclosure. As shown in FIG. 4, the outer edges 68 are generally parallel to the longitudinal direction 48 while the waist end edges 72 are generally parallel to the transverse axis 49. It should be understood, however, that in other aspects the outer edges 68 and/or the waist edges 72 may be slanted or curved as desired. Ultimately, the side panels 34 are generally aligned with a waist region 90 of the chassis 32.

The fastening system 80 may include laterally opposite first fastening components 82 adapted for refastenable engagement to corresponding second fastening components 84. In the aspect shown in the figures, the first fastening component 82 is located on the elastic side panels 34, while the second fastening component 84 is located on the front region 22 of the chassis 32. In one aspect, a front 22 or outer surface 30 of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects, the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material, or the like. One skilled in the art will recognize that the shape, density, and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the aspect shown in the figures, the fastening components 82, 84 are attached to the side panels 34 along the edges 68. In this aspect, the fastening components 82, 84 are not elastic or extendable. In other aspects, however, the fastening components 82, 84 may be integral with the side panels 34. For example, the fastening components 82, 84 may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

The materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded-carded webs or foams provided by elastomeric or polymeric materials. The outer cover 40, for instance, can be a single layer of a liquid impermeable material, or alternatively can be a multi-layered laminate structure in which at least one of the layers is liquid impermeable. In other aspects, however, it should be understood that the outer cover 40 may be liquid permeable. In this aspect, for instance, the absorbent article 20 may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., U.S.A., and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air-forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394 and Favor 9543 superabsorbents are available from DeGussa Superabsorbers located at Parsippany, N.J. U.S.A.

After being formed or cut into a desired shape, the absorbent web material may be wrapped or encompassed by a wrap sheet made from a suitable tissue or meltblown web. The wrap sheet aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 issued Jul. 11, 1978 to Richard A. Anderson, et al.; U.S. Pat. No. 5,284,703 issued Feb. 8, 1994 to Cherie H. Everhart, et al. and U.S. Pat. No. 5,350,624 issued Sep. 27, 1994 to William A. Georger, et al., which are incorporated herein by reference to the extent they are consistent (i.e., not in conflict) herewith.

A dryness indicator can be used in conjunction with an absorbent article, such as the one described herein, or in any other situation in which the duration of dryness needs to be determined. Use of a dryness indicator in conjunction with an absorbent article is described herein for exemplary purposes, but the uses of a dryness indicator are not limited to absorbent articles.

When the absorbent article 20 is insulted with a liquid, such as urine, menses, blood, or the like, the absorbent structure 44 captures and retains the liquid. Conventional absorbent articles 20 are so effective at retaining liquid that caregivers may not know when an absorbent article 20 has been insulted. With traditional products, the caregiver does not have any way of determining whether the absorbent article 20 has been insulted, or for how long the absorbent article 20 remained dry before it was insulted. A body fluid indication system including a dryness indicator 100 that is in liquid communication with either the absorbent structure 44, the liner 42, or both, addresses these issues.

The present disclosure is directed to incorporating a body-fluid-indicating system into a disposable absorbent article 20. In this regard, the absorbent article 20 includes a dryness indicator 100 positioned adjacent the liner 42. The body-fluid-indicating system is described herein in relation to the liner 42, but in other aspects the body-fluid-indicating system can be associated instead with the outer cover 40, with appropriate changes made to the description.

Figure 5:
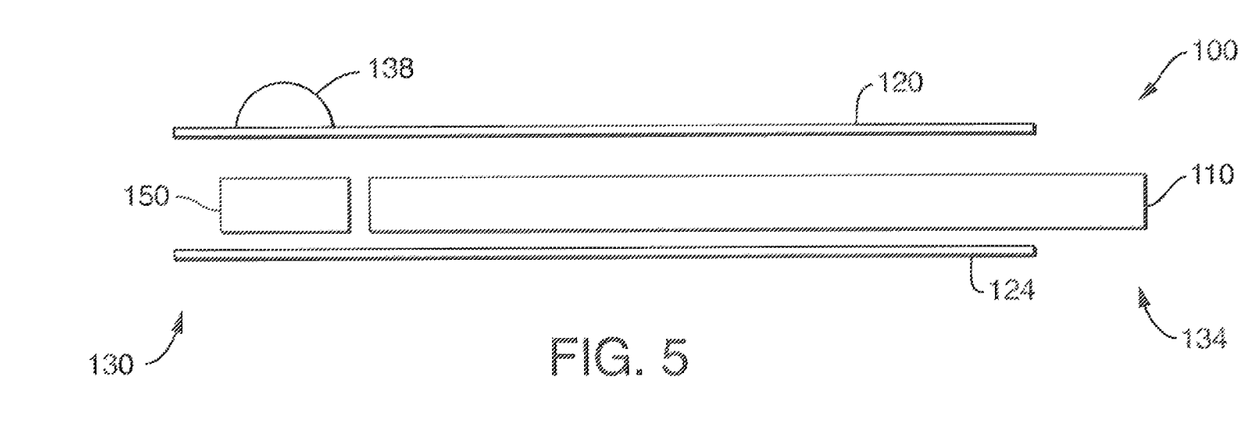
FIG. 5 is a cross sectional exploded schematic elevation view of a dryness indicator that can be used in conjunction with the absorbent article of FIG. 1.

FIG. 5 illustrates an example of the dryness indicator 100 described herein. The dryness indicator 100 includes a substrate or wicking strip 110. The substrate strip is protected by liquid impermeable top and bottom film layers 120, 124 on each side. The two ends of the strip are the reservoir end 130 and the open end 134. The reservoir end 130 of the strip 110 is a closed end, sealed between the top and bottom film layers 120, 124. The reservoir end 130 is in potential liquid communication with a reservoir 138. The reservoir 138 includes a non-reactive colored dye solution or colorant that is completely isolated from the strip 110 before the dryness indicator 100 is activated.

The wicking strip 110 can be any suitable material, such as a tissue, nonwoven layer, cellulosic materials, treated nonwovens, synthetic fibers, natural fibers, open-celled foam, or the like. Suitable material and construction of the wicking strip 110 can be chosen such that a liquid colorant will move slowly through the wicking strip 110. This speed at which a liquid moves through the wicking strip 110 can be measured using a standard vertical wicking test. The wicking strip 110 can have a vertical wicking speed of colorant of less than approximately 1.0 cm/hr, alternatively less than approximately 0.5 cm/hr, or alternatively less than approximately 0.1 cm/hr. The wicking strip 110 can have a vertical wicking speed of a water-based fluid of greater than approximately 1.0 cm/min, alternatively greater than approximately 3 cm/min, or alternatively greater than approximately 5 cm/min. Low wicking speed of the wicking strip 110 allows for relatively short dryness indicators 100 to be utilized to indicate relatively long durations from the time of activation.

The colorant and the wicking strip material can be selected to obtain any desired timing (t) ranges, including as examples $0.25<t<10$ hours, $0.50<t<6$ hours, and $1.0<t<3$ hours, although any suitable timing range can be used. The length (L) of the wicking strip 110 can also be varied to affect this range, with the range of lengths including $0.5<L<20$ cm, $1.0<L<10$ cm, and $2.0<L<6$ cm, although any suitable lengths range can be used. Additionally, flow rate (v) ranges for colorants can include $0.1<v<10$ cm/hour, $0.5<v<5$ cm/hour, and $1.0<v<2$ cm/hour, and for water-based fluid can include $0.1<v<10$ cm/min, $0.5<v<5$ cm/min, and $1.0<v<2$ cm/min, although any suitable flow rate ranges can be used.

The top and bottom film layers 120, 124 are generally liquid impermeable and at least one is generally translucent or transparent. The film layers 120, 124 can be constructed from, for example, polyethylene, polypropylene, polyester, or any material with similar properties. The film layers 120, 124 can also be a continuous strip or non-continuous if desired, or several strips or sections of film can also be used. The top film layer 120 can be formed with a pocket or reservoir 138 near the reservoir end 130 to contain colorant. In one aspect, a proper amount of colorant is sealed with a thin film layer such that the reservoir 138 is strong enough to keep the colorant from leaking before the product is used, while still being breakable by human finger pressure when the indicator 100 is to be activated.

In another aspect of the present application, the colorant is pre-encapsulated into a spherical reservoir through a liquid co-extrusion process in which the colorant is extruded as the core with a polymer melt as the wall/sheet. Similarly to the previous aspect, a pocket or reservoir 138 needs to be formed in the top film layer 120 to hold the colorant sphere, but the reservoir 138 need not be sealed with a film during the assembly of the dryness indicator 100.

In still another aspect of the present application, the dryness indicator 100 can include a fast distribution pad 150 between the reservoir 138 and the wicking strip 110 to help the colorant achieve an even colorant front upon contacting the wicking strip 110.

The open end 134 of the strip 110 is open to the exterior of the dryness indicator 100, and can therefore be placed in liquid communication with whatever object or surface is to be monitored. Upon a urine insult to the absorbent article 20, or a water-based fluid insult to any other object or surface, the water-based fluid (including urine) can enter the open end 134 of the dryness indicator 100, thereby wicking into the strip 110. As used herein, unreacted water-based fluid is a water-based fluid such as urine that enters into and travels along the wicking strip 110 in the same form in which it entered the absorbent article 20, object, or surface. Such water-based fluid has not been reacted with or acted upon by any gels, clays, or other substances, reactants, or chemicals.

The colorant is disposed in the reservoir 138. Experimentation demonstrated that water-based colorants were not sufficiently stopped by unreacted water-based fluid, and that the timing line 160 (see FIG. 6) could be indistinct and unstable over time. Because water-based colorants are undesirable due to the unclear cut off of the stopping time, an oil-based colorant system was developed. The oil-soluble colorants listed in Table 1 were prepared by dissolving 5 mg of dye in 1 mL of oil (mineral, extra virgin olive, avocado, canola, or corn) and screened. Solvent Blue 35 was chosen for its vibrant color.

TABLE 1

| | |
|---|---|
| D&C Green 6 | G6 |
| Sublaprint Blue 70044 | B700 |
| Sublaprint Red 70011 | R700 |
| Blue Pigmented Wax Dispersion | BPW |
| Magenta Pigmented Wax Dispersion | MPW |
| Blue Dye Wax Dispersion | BDW |
| Red Dye Wax Dispersion | RDW |
| Solvent Blue 59 | SB59 |
| Solvent Blue 35 | SB35 |

Figure 7:
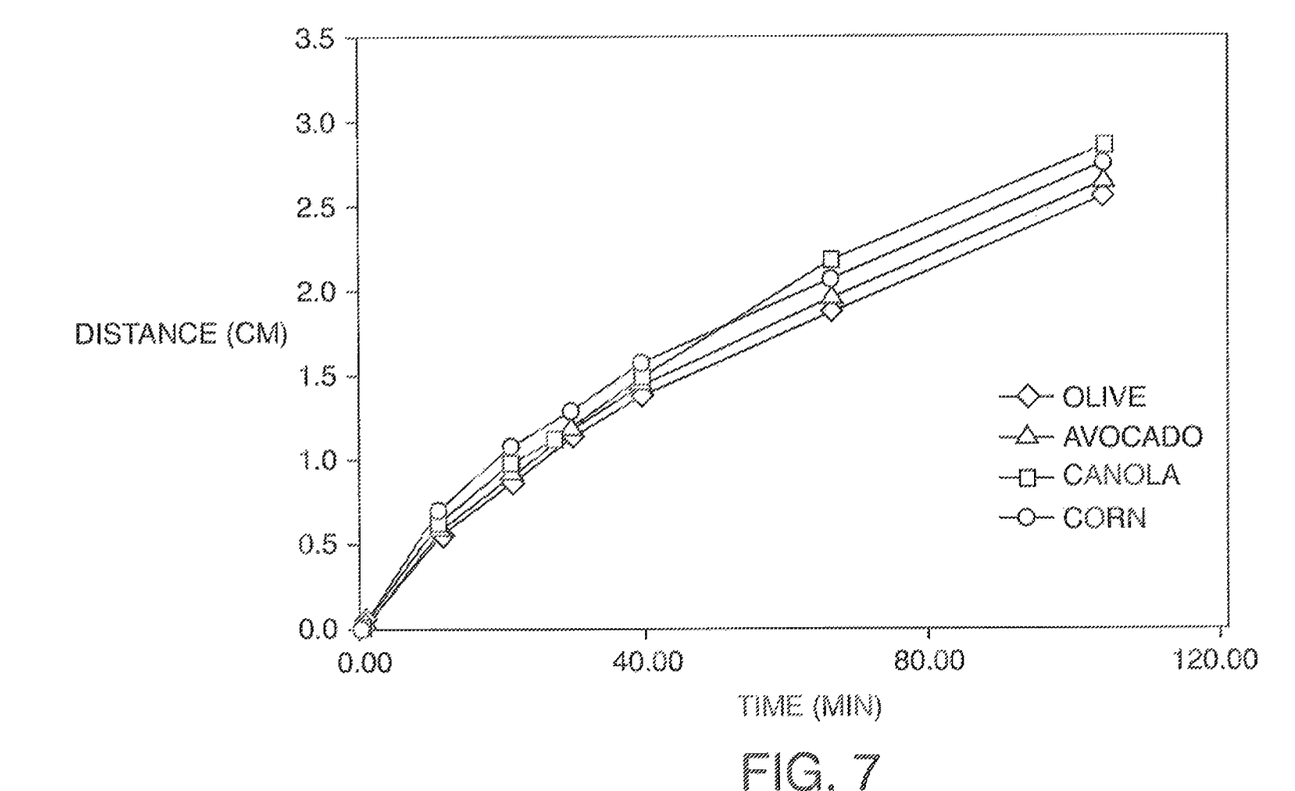
FIG. 7 illustrates the flow rate of SB35 colorant in various food oil bases.

In time tracking studies, 100 μl of SB 35 colorant solution was pipetted into 96 well plates, and a 6×0.5 cm² substrate strip was placed into the well. Results are illustrated in FIG. 7. Oil-soluble colorant diffuses through the strip 110 consistently in the time frame desirable for the dryness indicator 100.

In addition, different wicking strip substrates were investigated for their ability to wick an oil-based colorant. The substrates are listed in Table 2.

TABLE 2

| Substrate Name | Material | Manufacturer | Abbreviation |
| --- | --- | --- | --- |
| Filter Paper 3001-861 | Cellulose | Whatman | WFP |
| Filter Paper BVPP 12205 | Cellulose | VWR Brand Millipore | FP BVPP |
| 5.0 µm Hydrophilic PVDF | Poly(vinylidene fluorine) | Millipore | PVDF5 |
| 1.2 µm Hydrophilic PVDF | Poly(vinylidene fluorine) | Millipore | PVDF1.2 |
| 0.1 µm Hydrophilic PVDF | Poly(vinylidene fluorine) | Millipore | PVDF0.1 |
| Unisart CN 150 | Nitrocellulose | Sartorius Stedim Biotech | NC150 |
| Unisart CN 95 | Nitrocellulose | Sartorius Stedim Biotech | NC95 |
| Hi-Flow Plus 240 | Nitrocellulose | Millipore | NC240 |
| X-7744 | UHMW polyethylene | Porex | X-7744 |
| Hi-Flow Plus HFB 24004 | Nitrocellulose | Millipore | 24004 |
| NM87104 F500A0A | Nylon 6,6 | Cuno | Cuno |
| Accuwik Ultra | Hydrolyzed Polyester | Pall Corporation | Acc |

Figure 8:
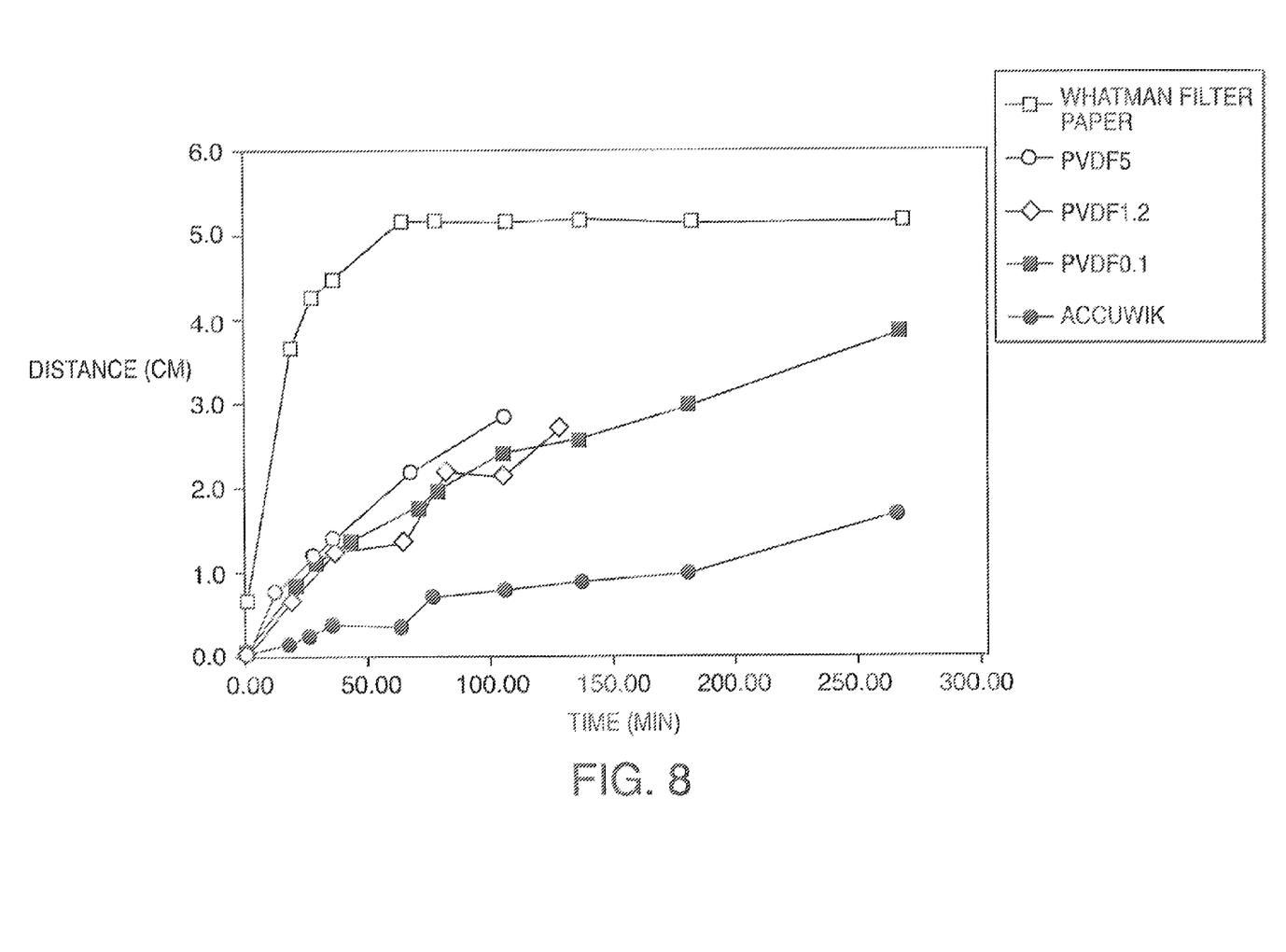
FIG. 8 illustrates the flow rate of an oil-based colorant in various wicking strip materials.
Figure 9:
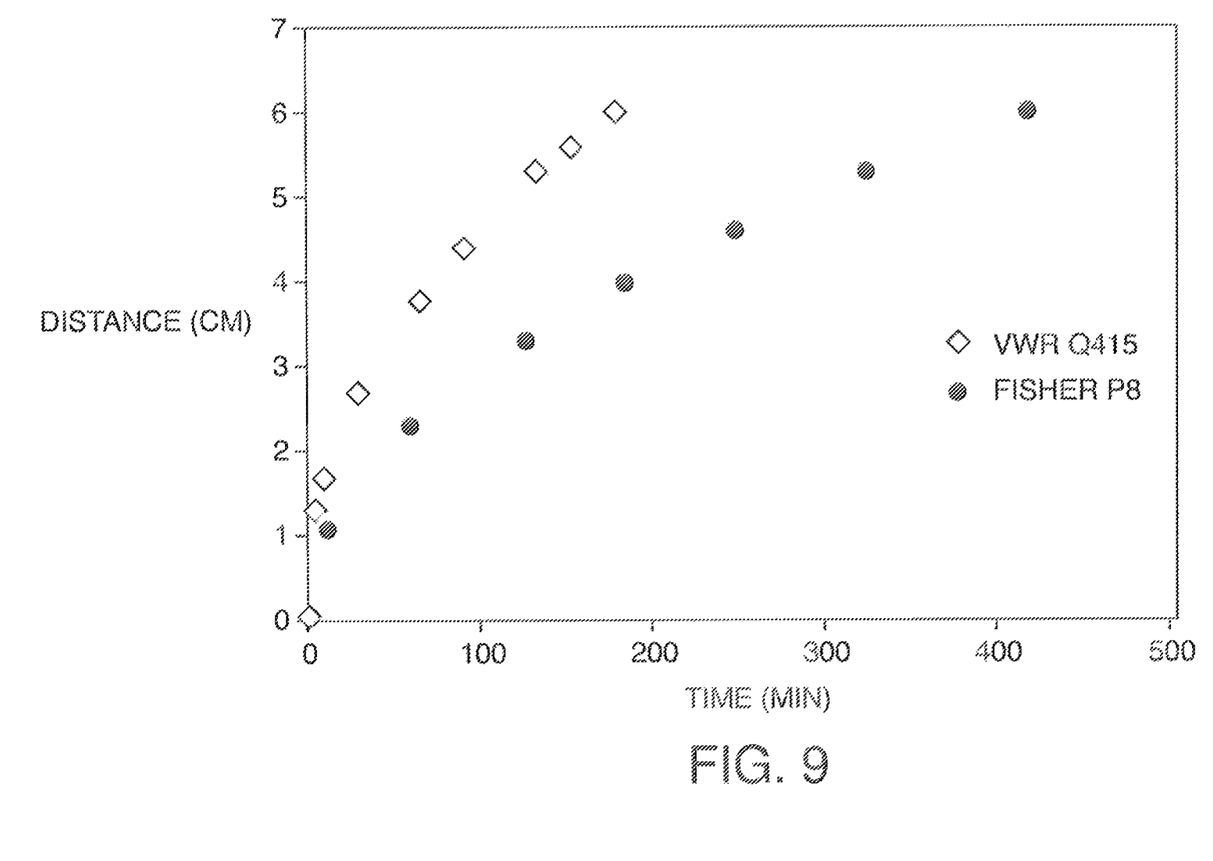
FIG. 9 illustrates the flow rate of an oil-based colorant in various wicking strip materials.

100 µl of SB 35 corn oil dye solution was pipetted into 96 well plates, and 6×0.5 cm² strips were placed into the wells. The colorant diffuses through strip 110 from one end at different speed depending on the types of substrates, indicating the choices and flexibility regarding the time frame the dryness indicator 100 is trying to indicate. Results are illustrated in FIGS. 8 and 9.

The dryness indicator 100 can be integrated onto the liner 42 of an absorbent article 20 in a manufacturing process or can be configured as a stand-alone unit such that a wearer, caregiver, or other user can place the dryness indicator 100 in or on an article, object, or surface.

In the case of use in conjunction with an absorbent article 20, all or a portion of the liner 42 adjacent the dryness indicator 100 can be translucent to facilitate detection of the dryness indicator 100 and active constituents. Alternatively, all or a portion of the liner 42 adjacent the dryness indicator 100 can be transparent.

In other aspects of the present disclosure, the absorbent article 20 includes a dryness indicator 100 positioned adjacent the outer cover 40. Any of the aspects, arrangements, and structures described herein may be applied to a dryness indicator 100 adjacent the outer cover 40 instead of the liner 42. The indicator material would consequently be visible through the outer cover 40 following an insult in much the same way as otherwise described herein.

When the dryness indicator 100 is activated by the wearer, caregiver, or other user, such as by breaking the separation between the colorant in the reservoir 138 and the reservoir end 130 of the strip 110, the colorant will flow to the strip 110 and wick from the reservoir end 130 toward the open end 134 of the strip 110 based on the capillary force, at a flow speed on the order of, for example, a centimeter per hour. The colorant position on the strip 110 tracks the passing of time.

Figure 6:
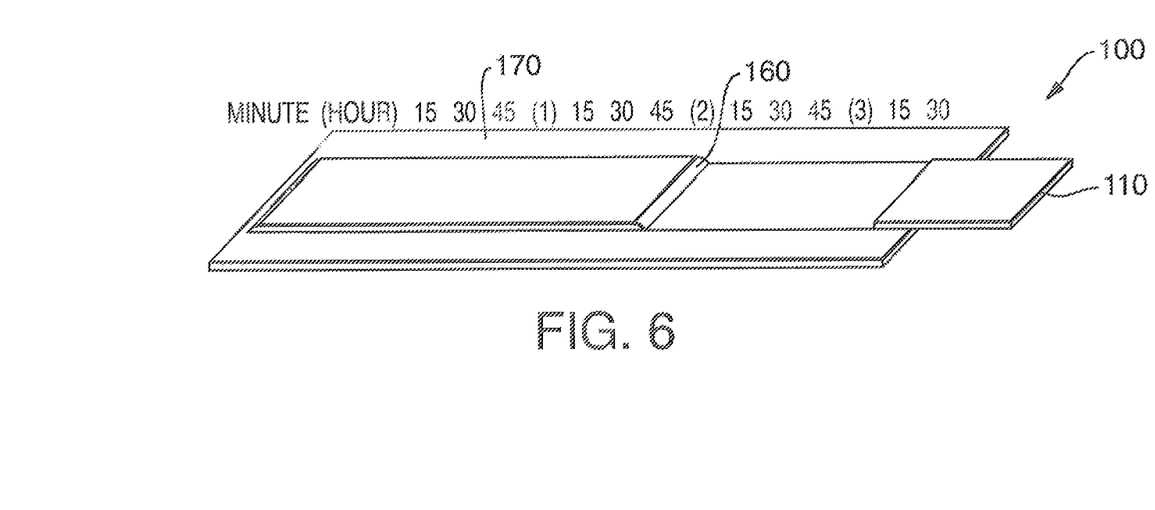
FIG. 6 is a perspective schematic view of one aspect of the dryness indicator of FIG. 5.

When a wearer urinates or the dryness indicator 100 is otherwise exposed to a water-based fluid, the water-based fluid will wick along the strip 110 at a much faster speed, on the order of, for example, three centimeters per minute, from the open end 134 of the strip 110 toward the reservoir end 130 of the strip 110. The water-based fluid will encounter the colorant at some point along the strip 110. When the water-based fluid front meets with the colorant front to define the timing line 160, the movement of the colorant and the water-based fluid will stop, because the capillary capacity of the strip 110 is by that point completely filled by either colorant or water-based fluid. The distance that the colorant traveled on the strip 110 indicates the dry time, which will be clearly embodied through a pre-calibrated distance-time scale 170 on the dryness indicator 100 or on the article 20 on or in which the dryness indicator 100 is disposed. An example of such a time scale is illustrated in FIG. 6.

Figure 10:
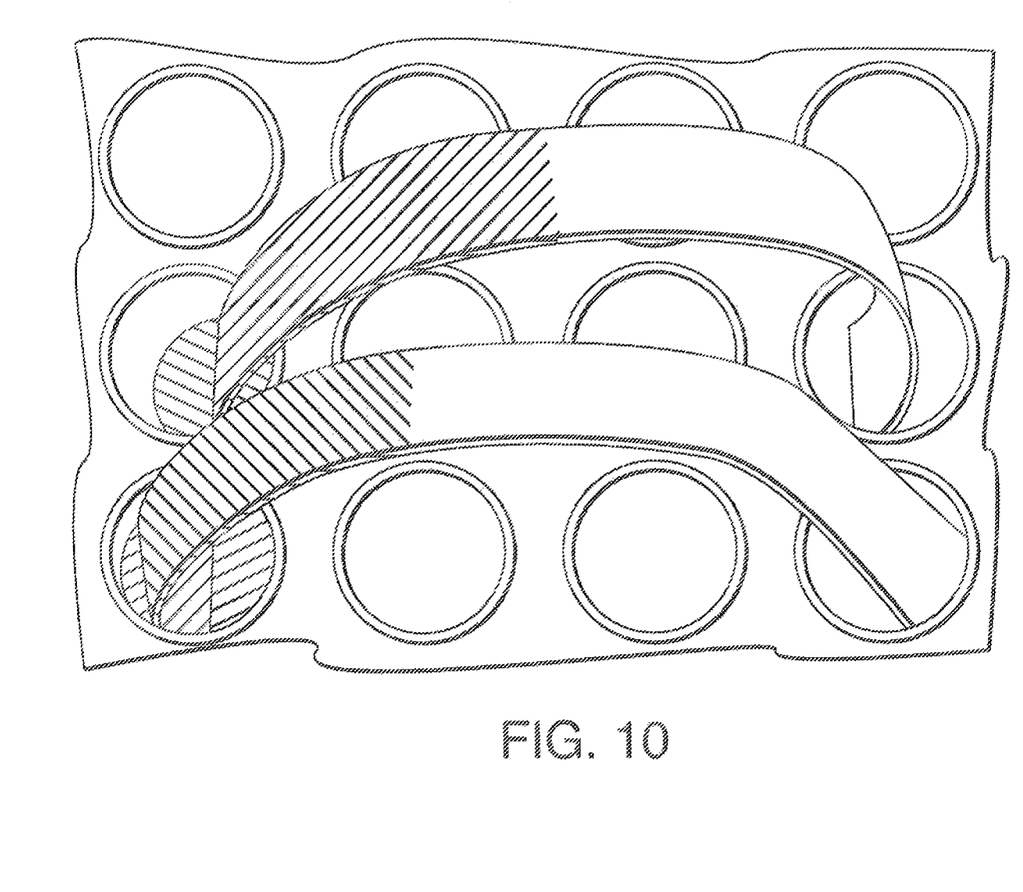
FIG. 10 illustrates the results of an oil-based colorant and a water-based fluid flowing in a wicking strip from opposite ends.

To demonstrate the stopping mechanism, 100 µl of SB 35 corn oil colorant solution was pipetted into 96 well plate, 6×0.5 cm² strips were placed into the wells to let the colorant diffuse from one end toward the other. Then synthetic urine was introduced from the other end of the strip 110 as shown in FIG. 10. The movement of the colorant stopped as soon as the synthetic urine met the colorant solution. More importantly, the timing line 160 remained sharp for several hours and no smearing was observed.

This dryness indicator 100 is beneficial to caregivers who are interested in knowing how long the wearer can hold urine, or in how long any given object or surface remained dry. In the case of a baby or toddler, this information can help parents decide if their baby or toddler is ready for potty training. The additional benefit to parents of a dryness indicator 100 is that the parents have a tool to use as a basis to reward their child for longer dry time diaper wearing.

An important aspect of the dryness indicator 100 is the inclusion of an activation mechanism to track time and a stop mechanism to essentially freeze time, each without the inclusion of reactants or other chemicals that can be problematic for the product safety of an absorbent article. Some prior art indicators have the ability to track time, although without a stop mechanism. Once they are activated, they cannot be stopped. Other indicators use gels, clays, or other substances or reactants in an attempt to influence the flow of urine. The dryness indicator 100 of the present application eliminates the need for any such substances by providing a hydraulic balance between colorant and a water-based fluid.

These and other modifications and variations to the present disclosure may be practiced by those of ordinary skill in the art, without departing from the spirit and scope of the present disclosure, which is more particularly set forth in the appended claims. In addition, it should be understood that aspects of the various aspects may be interchanged both in whole or in part. Furthermore, those of ordinary skill in the art will appreciate that the foregoing description is by way of example only, and is not intended to limit the disclosure as further described in such appended claims.

What is claimed is:

1. A dryness indicator comprising:
   a wicking strip linearly continuous between a reservoir end and an opposed open end;
   a liquid-impermeable top layer disposed on one side of the wicking strip;
   a liquid-impermeable bottom layer disposed on the opposite side of the wicking strip, wherein the top layer is affixed to the bottom layer to only partially enclose the wicking strip such that the open end of the wicking strip extends beyond one of the top and bottom layers, and wherein the indicator is configured such that the open end of the wicking strip can be placed in liquid communication with an object or surface; and
   a reservoir including an oil-based colorant with the potential to be in liquid communication with the reservoir end of the wicking strip, wherein the reservoir is sealed against exposure to water-based fluid and wherein the wicking strip is configured such that colorant wicking from the reservoir end and an unreacted water-based fluid wicking from the open end meet to define a timing line.

2. The indicator of claim 1, further comprising a time scale associated with the indicator and disposed on the indicator or the object or surface.

3. The indicator of claim 2, wherein the object is an absorbent article, and wherein the position of the timing line relative to the time scale indicates the time between a wearer donning the absorbent article and the wearer insulting the absorbent article.

4. The indicator of claim 1, wherein the wicking strip is free of substances with which the unreacted water-based fluid can chemically react.

5. The indicator of claim 1, wherein the colorant has a colorant wicking rate, wherein the unreacted water-based fluid has an unreacted water-based fluid wicking rate, and wherein the unreacted water-based fluid wicking rate is faster than the colorant wicking rate.

6. The indicator of claim 1, wherein the indicator is configured to allow a wearer, caregiver, or user to cause the release of colorant from the reservoir to the wicking strip.

7. The indicator of claim 6, wherein the release is caused by squeezing the reservoir.

8. The indicator of claim 6, wherein the release is caused by rupturing a portion of the reservoir.

9. The indicator of claim 1, wherein the object is a disposable absorbent article.

10. The indicator of claim 1, wherein the water-based fluid is urine.

11. A hydraulically-controlled dryness indicator, the indicator comprising:
    a wicking strip linearly continuous between a reservoir end and an opposed open end and only partially enclosed within a top layer is affixed to a bottom layer such that the open end of the wicking strip extends beyond one of the top and bottom layers, and wherein the indicator is configured such that the open end of the wicking strip can be placed in liquid communication with an object or a surface; and
    a reservoir including an oil-based colorant with the potential to be in liquid communication with the reservoir end of the wicking strip, wherein the reservoir is sealed against exposure to water-based fluid, wherein the wicking strip is configured such that colorant wicking from the reservoir end and unreacted water-based fluid wicking from the open end meet to define a timing line, and wherein the wicking strip is free of substances with which the unreacted water-based fluid can chemically react.

12. The indicator of claim 11, further comprising a time scale associated with the indicator and disposed on the indicator or the object or surface.

13. The indicator of claim 12, wherein the object is an absorbent article, and wherein the position of the timing line relative to the time scale indicates the time between a wearer donning the absorbent article and the wearer insulting the absorbent article.

14. The indicator of claim 11, wherein the water-based fluid is urine.

15. The indicator of claim 11, wherein the colorant has a colorant wicking rate, wherein the unreacted water-based fluid has an unreacted water-based fluid wicking rate, and wherein the unreacted water-based fluid wicking rate is faster than the colorant wicking rate.

16. The indicator of claim 11, wherein the indicator is configured to allow a wearer, caregiver, or user to cause the release of colorant from the reservoir to the wicking strip.

17. A disposable absorbent article for absorbing a liquid, the absorbent article comprising:
    a chassis including a liner, an outer cover, and an absorbent structure positioned between the liner and the outer cover, the chassis including a crotch region positioned in between a front region and a back region, the front region and the back region defining a waist region therebetween; and
    a dryness indicator positioned adjacent the liner or the outer cover, the dryness indicator including
        a wicking strip linearly continuous between a reservoir end and an opposed open end;
        a liquid-impermeable top layer disposed on one side of the wicking strip;
        a liquid-impermeable bottom layer disposed on the opposite side of the wicking strip, wherein the top layer is affixed to the bottom layer to only partially enclose the wicking strip such that the open end of the wicking strip extends beyond one of the top and bottom layers, and wherein the indicator is configured such that the open end of the wicking strip can be placed in liquid communication with a disposable absorbent article; and
        a reservoir including an oil-based colorant with the potential to be in liquid communication with the reservoir end of the wicking strip, wherein the reservoir is sealed against exposure to water-based fluid and wherein the wicking strip is configured such that colorant wicking from the reservoir end and unreacted urine wicking from the open end meet to define a timing line.

18. The absorbent article of claim 17, further comprising a time scale associated with the indicator and disposed on the indicator or the absorbent article.

19. The absorbent article of claim 17, wherein the indicator is configured to allow a wearer, caregiver, or user to cause the release of colorant from the reservoir to the wicking strip.

* * * * *